United States Patent [19]

Porret et al.

[11] 3,978,076

[45] *Aug. 31, 1976

[54] DIALKOXYPHOSPHONOALKYL DERIVATIVES OF CYCLIC UREIDES

[75] Inventors: Daniel Porret, Binningen; Jürgen Habermeier, Pfeffingen, both of Switzerland

[73] Assignee: Ciba-Geigy Corporation, Ardsley, N.Y.

[ * ] Notice: The portion of the term of this patent subsequent to Dec. 9, 1992, has been disclaimed.

[22] Filed: May 5, 1975

[21] Appl. No.: 574,798

Related U.S. Application Data

[62] Division of Ser. No. 419,313, Nov. 27, 1973, Pat. No. 3,892,765.

[30] Foreign Application Priority Data

Dec. 12, 1972 Switzerland.................... 18030/72

[52] U.S. Cl............................ 260/309.5; 260/2 EP
[51] Int. Cl.$^2$........................................ C07D 49/32
[58] Field of Search................................ 260/309.5

[56] References Cited
UNITED STATES PATENTS

3,741,978  6/1973  Jamison........................... 260/309.5

*Primary Examiner*—Ethel G. Love
*Attorney, Agent, or Firm*—Vincent J. Cavalieri

[57] ABSTRACT

The invention relates to 3-dialkoxyphosphonoalkyl-hydantoins and 3-dialkoxyphosphonoalkyl-dihydrouracils. These compounds are manufactured by reacting the hydantoins or dihydroaracils substituted in 3-position by a halogenalkyl group with a trialkyl phosphite. They can be incorporated into polymeric materials or their starting substances and impart to them non-inflammability.

6 Claims, No Drawings

DIALKOXYPHOSPHONOALKYL DERIVATIVES OF CYCLIC UREIDES

This is a divisional of application Ser. No. 419,313, filed on Nov. 27, 1973, now U.S. Pat. No. 3,892,765, which issued on July 1, 1975.

The invention relates to 3-dialkoxyphosphonoalkyl-hydantoins and 3-dialkoxyphosphonoalkyl-dihydroxyuracils, processes for their manufacture and the use of these compounds for flameproofing plastics.

Phosphorus-containing flame-retarding agents are already known. To achieve an advantageous effect, considerable amounts of these agents, in most cases more than 10%, must be added to the plastics to be protected, but this frequently has an adverse effect on the protected plastics in other respects, for example mechanical respects. It has now been found that the phosphorus-containing compounds according to the invention render plastics non-inflammable if they are added in such amounts that the phosphorus content is at least 0.8 – 4%.

The compounds according to the invention correspond to the formulae I and I'

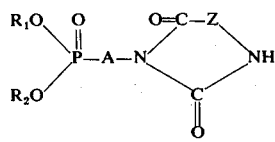   (I)

and

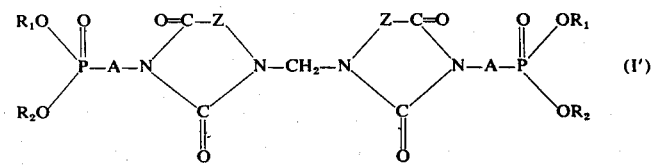   (I')

in which Z denotes a nitrogen-free divalent radical which is required to complete a 5-membered or 6-membered heterocyclic ring, A denotes an alkylene group with 1–12 carbon atoms which is optionally interrupted by oxygen atoms and $R_1$ as well as $R_2$ each denote an alkyl or alkenyl group which can be substituted, for example by halogen, or together denote an alkylene group with 2–5 carbon atoms.

Z preferably represents a methylene group which can be substituted by alkyl groups with 1 to 6 carbon atoms or a cycloalkyl group, such as the methylene group or especially the propylidene-(2,2) group, also the n- or iso-propylmethylene group or, in the case of the compounds of the formula I, the cyclohexylidene group or cyclopentylidene group or, in the case of the compounds of the formulae I and I', an ethylene group which is optionally substituted by alkyl groups with 1 to 4 carbon atoms, such as the ethylene, 1,2-dimethylethylene, 2,2-dimethylethylene or 1-methyl-2-isopropyl-ethylene group.

$R_1$ and $R_2$ each preferably denote an alkyl or alkenyl group with 1 to 4 carbon atoms, especially the methyl or ethyl group, but also the propyl, butyl, allyl, butenyl or monochloroethyl group.

A preferably denotes an alkylene group with 2 to 6 carbon atoms, especially the ethylene group, or the radical of a diethyl ether.

The compounds according to the invention are manufactured by reacting compounds of the formulae II or II'

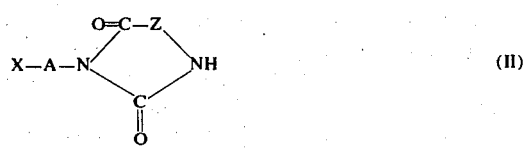   (II)

or

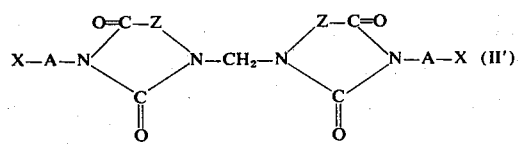   (II')

In which X denotes chlorine or bromine, with a trialkyl phosphite of the formula III

   (III)

wherein $R_3$ denotes an optionally substituted alkyl or alkenyl group.

For the reaction, which corresponds to a Michaelis-Arbusow reaction, the mixture is usually warmed for several hours to above 100°C, preferably 120°–160°C, in the course of which $R_3X$ distils off. $R_3X$ is, for example, methyl chloride, ethyl chloride, butyl chloride or 1,2-dichloroethane.

The compounds of the formulae II and II' are obtained by reaction of the corresponding hydantoins or dihydrouracils, which are unsubstituted in the 3-position, with a compound of the formula IV $$X-A-X \quad (IV)$$

in the presence of agents which split off hydrogen halide, such as alkalis or strongly basic salts, for example sodium carbonate. Compounds of the formula IV are, for example, β,β'-dichloroethane or β,β'-dichlorodiethyl ether.

The products according to the invention are liquid to crystalline substances which are colourless in the pure state. They can be purified by recrystallisation or vacuum distillation.

When incorporated into polymers or their starting substances, they impart non-inflammability to these materials. If they still contain an active hydrogen atom (compounds of the formula I), they can be glycidylated, methylolated and subjected to other reactions, for example the formation of adducts with epoxide resins.

They can be added, for example, to epoxide resin/- curing agent mixtures before the curing reaction is carried out. They can also be incorporated into the polymeric material by kneading, for example by solution or suspension in a solvent or dispersing agent, such as methanol, ethanol or acetone, mixing of this solution or suspension with the powdered polymer and removal of the solvent or suspending medium. The effective amount of substance according to the invention depends on the material to be protected and on the structure of the compound containing phosphorus. However, the effective minimum amount is surprisingly low: in general, a phosphorus content of 2 to 4% in the material already suffices to make the material non-inflammable.

Manufacture of the Starting Substances

A: 3-(β-Chloroethyl)-5,5-dimethyl-hydantoin

A mixture of 1,664 g of 5,5-dimethyl-hydantoin (13.0 mols), 897 g of anhydrous potassium carbonate (6.5 mols), 5,148 g of 1,2-dichloroethane (52 mols) and 1,485 ml of dimethylformamide is reacted for 18 hours and 20 minutes at 90°C to 100°C internal temperature (external temperature 155°C), the water of reaction produced being removed continuously by azeotropic circulatory distillation. Water of reaction split off: 110 g (94.0% of theory). Thereafter, the reaction mixture, whilst still hot, is separated by filtration from the potassium chloride produced, the filtrate is concentrated on a rotary evaporator at 100°C in a water pump vacuum and the residue is dried to constant weight at 100°C and 10⁻¹ mm Hg.

2,385 g of a clear, brown, highly viscous substance (96.2% of theory) are obtained.

The crude product if distilled at 0.1 to 0.2 mm Hg and 146°–149°C: 2,068.3 g yield of pure substance (83.4% of theory). A sample recrystallised from ethanol melts at 95.8° to 96.2°C and displays the following analytical data:

| calculated: | 44.13% C | 5.91% H | 14.67% N | 18.54% Cl |
|---|---|---|---|---|
| found: | 44.10% C | 5.82% H | 14.70% N | 18.60% Cl. |

B: 3-(β-Chloroethyl)-5-methyl-5-ethyl-hydantoin 284.3 g of 5-methyl-5-ethyl-hydantoin (2.0 mols), 138.2 g of anhydrous potassium carbonate (1.0 mol), 791.7 g of 1,2-dichloroethane (8.0 mols) and 230 ml of dimethylformamide are subjected to an azeotropic circulatory distillation, analogously to A, for 25 hours at 90°C to 107°C internal temperature (external temperature: 160°C). After completion of the reaction, the mixture is filtered whilst still hot and the filtrate is concentrated on a rotary evaporator at 90°C under a water pump vacuum. The reaction mixture is then dried to constant weight at 90°C and 10⁻¹ mm Hg. 392.5 g. of a brown, clear product (95.9% of theory) are obtained, and purified by vacuum distillation (boiling point₀.₂: 147°C). Yield of pure material: 327.3 g (80% of theory). A sample recrystallised from diethyl ether melts at 58.0°C to 59.0°C.

Analytical data:

| calculated: | 47.23% C | 6.56% H | 13.61% N | 17.36% Cl |
|---|---|---|---|---|
| found: | 46.95% C | 6.40% H | 13.69% N | 17.32% Cl. |

C: 3-(β-Chloroethyl)-5,5-pentamethylene-hydantoin 336.4 g of 5,5-pentamethylene-hydantoin (2.0 mols), 138.2 g of anhydrous potassium carbonate (1.0 mol), 791.7 g of 1,2-dichloroethane (8.0 mols) and 300 ml of dimethylformamide are reacted analogously to A. After a reaction time of 21¾ hours at 101° to 117°C internal temperature (external temperature: 160°C) the reaction is complete and the reaction mixture is filtered whilst still hot. The filtrate is worked up analogously to A. 460.8 g of a brownish crystalline product (99.86% of theory) of melting point 154° to 156.4°C are obtained. Recrystallisation of the crude product from toluene in the ratio of 1:1.6 gives the pure compound, of melting point 156°–158°C, in 86% yield.

Microanalysis:

| calculated: | 51.83% C | 6.67% H | 12.27% N | 15.11% Cl |
|---|---|---|---|---|
| found: | 52.06% C | 6.55% H | 12.14% N | 15.37% Cl. |

The 60 Mc H-NMR spectrum is consistent with the following structure:

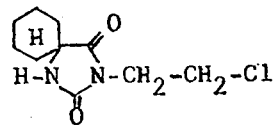

D: 3-(6-Chloro-n-hexyl)-5,5-dimethyl-hydantoin 128 g of 5,5-dimethyl-hydantoin (1.0 mol), 69 g of anhydrous potassium carbonate (0.5 mol) and 775 g of 1,6-dichlorohexane are reacted at 132°–150°C internal temperature (external temperature 160°C) and the resulting water of reaction is removed continuously by azeotropic circulatory distillation. After 6 hours 25 minutes, the reaction is complete and the reaction mixture is filtered hot to remove the potassium chloride formed. The filtrate is concentrated on a rotary evaporator and dried to constant weight at 100°C and 10⁻¹ mm Hg.

224 g of a brown highly viscous crude product (90.8% of theory) are obtained, and purified by vacuum distillation (boiling point₀.₀₂ = 136°–151°C). Yield of pure substance: 152.7 g (61.9% of theory).

Melting point: 39.8° to 44°C.

Chlorine content: 12.69% Cl.

E. 3-(3-Oxa-5-chloro-pentyl)-5,5-dimethyl-hydantoin 640 g of 5,5-dimethyl-hydantoin (5.0 mols), 345.5 g of anhydrous potassium carbonate (2.5 mols) and 2,860 g of β,β'-dichloroethyl ether (20.0 mols) are subjected to an azeotropic circulatory distillation for 6 hours 20 minutes at 121° to 152°C internal temperature (external temperature 170°C). Working up takes place analogously to A and 994 g of a brown, viscous crude product (84.7% of theory) are obtained. Vacuum distillation and subsequent recrystallisation in diethyl ether gives pure β-chloro-β'-(5,5-dimethyl-hydantoinyl-3)-diethyl ether [or 3-(3-oxa-5-chloro-pentyl)-5,5-dimethyl-hydantoin] of melting point 55.4° to 57.4°C.

Elementary analysis:

| calculated: | 45.99% C | 6.41% H | 11.73% N | 14.92% Cl |
|---|---|---|---|---|
| found: | 46.06% C | 6.44% H | 11.94% N | 15.11% Cl |

F: 3-(4-Chlorobutyl)-5,5-dimethyl-hydantoin

A mixture of 538 g of 5,5-dimethyl-hydantoin (4,2 mols), 290 g of anhydrous potassium carbonate (2.1 mols) and 2,130 g of 1,4-dichlorobutane (16.77 mols) is reacted analogously to A for 8 hours at 138° to 141°C internal temperature (external temperature 200°C). Working up takes place analogously to A and 830.9 g of a brown viscous crude product (90.5% of theory) are obtained, and are purified by vacuum distillation (boiling point$_{0.2}$: 151°–153°C) and subsequent recrystallisation from diethyl ether. The pure product melts at 54.4° to 56.3°C.

Analytical data:

| calculated: | 49.26% C | 7.02% H | 3.1 % N | 15.72% Cl |
|---|---|---|---|---|
| found: | 49.43% C | 6.91% H | 12.81% N | 16.21% Cl. |

EXAMPLES

EXAMPLE 1

3-(Dimethoxyphosphonoethyl)-5,5-dimethyl-hydantoin

A mixture of 381.3 g of 3-(2'-chloroethyl)-5,5-dimethyl-hydantoin (2.0 mols) [manufactured according to A] and 322.6 g of trimethyl phosphite (2.6 mols) is reacted at 120°C (bath temperature 180°C). The methyl chloride produced in the reaction is condensed in a cold trap at −80° for the purpose of following the course of the reaction. After 39 hours, the reaction is complete, at which stage the internal temperature has risen to 190°C, and 96.7 g of methyl chloride (95.7% of theory) are obtained. The reaction product is freed of readily volatile constituents in a water pump vacuum at 110°C and is subsequently dried to constant weight at $10^{-1}$ mm Hg and 105°C.

490 g of a yellowish, clear, highly viscous crude product (92.7% of theory) are obtained, displaying the following analytical data: 9.80% of phosphorus and ≤ 0.2% of chlorine.

A crude product purified by distillation from a bulb tube (at 140°–160°C external temperature and $10^{-1}$ mm Hg) and subsequent crystallisation from ethyl acetate melts at 101.2°–102.6°C.

Elementary analysis:

| calculated: | 40.93% C | 6.72% H | 10.54% N | 11.65% P |
|---|---|---|---|---|
| found: | 40.91% C | 6.49% H | 10.60% N | 11.72% P |

The H-NMR spectrum is consistent with the following structure:

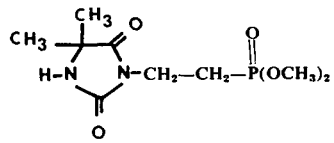

EXAMPLE 2

3-(Diethoxyphosphono-n-butyl)-5,5-dimethyl-hydantoin 43.9 g of 3-(4-chloro-n-butyl)-5,5-dimethyl-hydantoin (0.2 mol) [manufactured according to F] and 39.9 g of triethyl phosphite are reacted analogously to Example 1 for 31 hours at 163 to 205°C (bath temperature 184° to 220°C), ethyl chloride being split off. The mixture is worked up analogously to Example 1 and 60.1 g of a clear, yellow, viscous substance (93.9% of theory) are obtained.

Analytical data: 8.95% P, <0.3% chlorine.

Distillation from a bulb tube (external temperature: 140° to 160°C and 0.03 mm Hg) gives a clear, colourless, viscous distillate with the following analytical data:

Elementary analysis:

| calculated: | 48.69% C | 7.74% H | 8.97% N | 9.47% P |
|---|---|---|---|---|
| found: | 48.74% C | 7.87% H | 8.75% N | 9.67% P. |

EXAMPLE 3

3-(Diethoxyphosphonoethyl)-5-methyl-5-ethyl-hydantoin 102.3 g of 3-(2-chloroethyl)-5-methyl-5-ethyl-hydantoin (0.5 mol) [manufactured according to B] and 99.8 g of triethyl phosphite (0.6 mol) are reacted analogously to Example 1 at 161° to 182°C. The reaction mixture is worked up analogously to Example 1 and 127 g of light yellow, clear, viscous substance (83% of theory) are obtained. Distillation from a bulb tube (external temperature: 148°C to 160°C; 0.04 mm Hg) gives a colourless, viscous distillate which displays the following analytical data:

Elementary analysis:

| calculated: | 47.15% C | 7.79% H | 9.22% N | 10.04% P |
|---|---|---|---|---|
| found: | 47.06% C | 7.57% H | 9.15% N | 10.11% P. |

EXAMPLE 4

3-(Diethoxyphosphono-n-hexyl)-5,5-dimethyl-hydantoin 24.7 g of 3-(6-chloro-n-hexyl)-5,5-dimethyl-hydantoin (0.1 mol) [manufactured according to D] and 21.6 g of triethyl phosphite (0.13 mol) are reacted for 85 hours at 150°C to 192°C. After working up the mixture analogously to Example 1, 34.0 g of a yellow, viscous substance (97.7% of theory), containing 9.8% of phosphorus, are obtained.

EXAMPLE 5

β-(Dimethoxyphosphono)-β'-(5,5-dimethyl-hydantoin-3-yl)-diethyl ether 70.4 g of β-chloro-β'-(5,5-dimethyl-hydantoin-3-yl)-diethyl ether (0.3 mol) [manufactured according to E] and 48.4 g of trimethyl phosphite are reacted for 48 hours and 25 minutes at 120°C to 189°C bath temperature. After 48 hours and 25 minutes the reaction is complete and 14.9 g of methyl chloride (98.3% of theory) have been split off. The mixture is worked up analogously to Example 1 and 84.3 g of a clear, yellow, viscous product (91.1% of theory) are obtained, displaying the following analytical data: 8.70% phosphorus and <0.3% chlorine.

EXAMPLE 6

3-(Dimethoxyphosphonoethyl)-5,5-pentamethylene-hydantoin 48.4 g of trimethyl phosphite (0.39 mol) are added dropwise over the course of 115 minutes to 69.3 g of 3-(2-chloroethyl)-5,5-pentamethylene-hydantoin (0.3 mol) [manufactured according to C] at 165° to 170°C. After 20 hours and 45 minutes, the elimination of methyl chloride has ceased. The reaction mixture is worked up as described in Example 1 and 84.3 g of a solid, yellow product (92.3% of theory) are obtained, containing 8.9% phosphorus and <0.3% chlorine.

EXAMPLE 7

3-(Diethoxyphosphonoethyl)-5,5-dimethyl-hydantoin 704.1 g of 3-(2-chloroethyl)-5,5-dimethyl-hydantoin (3.0 mols) [manufactured according to A] and 598.5 g of triethyl phosphite are stirred at 162° to 188°C. The elimination of ethyl chloride has ceased after 22 hours and 20 minutes and the reaction product is worked up analogously to Example 1. 859.8 g of a yellow, clear, viscous substance (98.0% of theory), of 8.6% phosphorus content, are obtained.

Use example 200 g of a technically manufactured triglycidyl compound from 1,3-bis-(5,5-dimethyl-hydantoinyl-3)-propan-2-ol, having an epoxide content of 6.1 epoxide equivalents/kg, and 133.3 g of 3-(dimethoxyphosphonoethyl)-5,5-dimethyl-hydantoin (0.505 mol) from Example 1 are stirred at 156° – 159°C internal temperature (bath temperature 180°C). The reaction is followed by continuously determining the epoxide content. After 35 minutes' reaction time the epoxide content is 3.0 epoxide equivalents/kg and after 90 minutes it is 2.58 epoxide equivalents/kg. The reaction is complete after 125 minutes and the reaction product is cooled to room temperature by pouring out onto a metal sheet. A brownish, brittle, somewhat tacky resin having an epoxide content of 2.26 epoxide equivalents/kg is obtained in practically quantitative yield (theory: 333.3 g). The phosphorus content is 3.98% P.

The IR spectrum shows, through the absence of the NH bands and the presence of the OH bands, that the reaction has taken place as desired.

100 g of the epoxide resin adduct thus produced are stirred with 33.0 g of hexahydrophthalic anhydride at 120°C and the clear, yellowish mixture is poured into aluminium moulds of sizes 120×120×4 mm and 120×15×10 mm which have been prewarmed to 120°C.

The curing takes place in 2 hours at 120°C and 16 hours at 150°C. The mouldings thus obtained have the following properties:

| | |
|---|---|
| Phosphorus content: | 3.0% P |
| Flexural strength (VSM 77,103): | 9.1–12.8 kg/mm² |
| Deflection (VSM 77,103): | 3.7–4.0 mm |
| Impact strength (VSM 77,105): | 9.0–15.5 cmkg/cm² |
| Heat distortion point according to Martens (DIN) | 77°C |
| Inflammability according to CTM 20* | Level 1/1" |

A horizontally clamped DIN standard bar (120×15×10 mm) of the plastic to be tested is exposed for 1 minute to the flame of a Bunsen burner fed with town gas and inclined at 45° (burner orifice: 9 mm, flame height with burner vertical: 10 cm), so that the 15 mm wide surface of the test specimen is 3 cm above the upper edge of the burner and the end face is at a horizontal distance of 1 cm from the lower edge of the burner.

What we claim is:

1. A dialkoxyphosphonoalkyl derivative of the formula

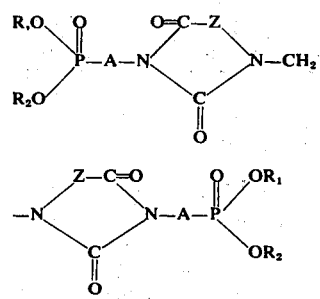

wherein Z is methylene, methylene substituted by alkyl of 1–6 carbon atoms, cyclopentylidene, or cyclohexylidene, $R_1$ and $R_2$ is alkyl or alkenyl of 1 to 4 carbon atoms, alkyl or alkenyl of 1 to 4 carbon atoms substituted by chloro, or $R_1$ and $R_2$ together form an alkylene of 2–5 carbon atoms, and A is alkylene of 1–12 carbon atoms, or diethylene ether.

2. A compound according to claim 1, in which Z denotes the propylidene-(2,2) group.

3. A compound according to claim 1, in which Z denotes the cyclohexylidene group.

4. A compound according to claim 1, in which $R_1$ and $R_2$ each denote an alkyl or alkenyl group with 1 to 4 carbon atoms.

5. A compound according to claim 1, in which $R_1$ and $R_2$ denote the ethyl or methyl group.

6. A compound according to claim 1, in which A denotes an alkylene group with 2 to 6 carbon atoms, especially the ethylene group, or the radical of diethyl ether.

* * * * *